US005633502A

United States Patent [19]
Fischione

[11] Patent Number: 5,633,502
[45] Date of Patent: May 27, 1997

[54] PLASMA PROCESSING SYSTEM FOR TRANSMISSION ELECTRON MICROSCOPY SPECIMENS AND SPECIMEN HOLDERS

[75] Inventor: Paul E. Fischione, Export, Pa.

[73] Assignee: E. A. Fischione Instruments, Inc., Export, Pa.

[21] Appl. No.: 515,271

[22] Filed: Aug. 11, 1995

[51] Int. Cl.$^6$ .............................. H01J 37/18; H01J 37/30
[52] U.S. Cl. ............................ 250/441.11; 250/452.1; 250/440.11; 315/111.21
[58] Field of Search .................... 250/306, 311, 250/440.11, 492.1, 423 R, 441.11; 315/111.21, 111.81

[56] References Cited

U.S. PATENT DOCUMENTS

| | | | |
|---|---|---|---|
| 4,859,908 | 8/1989 | Yoshida et al. | 315/111.21 |
| 4,902,934 | 2/1990 | Miyamura et al. | 315/111.21 |
| 5,137,063 | 8/1992 | Foster et al. | 250/441.11 |
| 5,217,053 | 6/1993 | Foster et al. | 250/441.11 |
| 5,273,609 | 12/1993 | Moslehi | 315/111.21 |
| 5,312,519 | 5/1994 | Sakai et al. | 250/441.11 |
| 5,368,685 | 11/1994 | Kumihashi et al. | 156/643 |
| 5,510,624 | 4/1996 | Zaluzec | 250/441.11 |
| 5,539,211 | 7/1996 | Ohtoshi et al. | 250/441.11 |

OTHER PUBLICATIONS

Richard S. Thomas & John R. Hollohan, "Use of Chemically–Reactive Gas Plasmas in Preparing Specimens for Scanning Electron Probe Microanalysis," Proceeding of the Seventh Annual Electron Microscope Symposium, Scanning Electron Microscopy, pp. 84–89, 1974. no month.

H. W. Zandbergen, et al., "The Use of Plasma–Cleaning for the Preparation of Clean Electron Transparent Thin Foils," Proceedings of the XIII International Congress for Electron Microscopy, vol. 1, pp. 1003–1004, 1994. no month.

O. O. Ajayi, et al., "Plasma Etching of Structural Ceramics for Microstructural Analysis," Submitted to National Science & Engineering Journal, Sep. 1992. no month.

SPI Supplies Brochure. no date.

The Center for the Industrial Applications of Plasmas and Beams Brochure. no date.

Primary Examiner—Bruce C. Anderson
Attorney, Agent, or Firm—Barry I. Friedman; Dickie, McCamey & Chilcote, P.C.

[57] ABSTRACT

A plasma processing method and apparatus are disclosed in which a low energy, high frequency plasma is utilized to remove both amorphous damage resulting from various specimen preparation techniques and contamination, mainly in form of hydrocarbons, from transmission electron microscopy specimens and specimen holders. The system comprises a vacuum system, a plasma chamber into which the specimen and the specimen holder are inserted, a housing having an access port with removable inner sleeve components, and a high frequency power supply which is coupled to the plasma chamber and enables both the generation and maintenance of the plasma. The inner sleeve components are preferably capable of accepting specimen holders produced by all manufacturers of transmission electron microscopes. In the preferred embodiment, the vacuum system comprises an oil-free vacuum system. To commence processing, the vacuum system is engaged for the evacuation of the plasma chamber for subsequent formation of the plasma. Processed gas may be introduced into the plasma chamber through the automated operation of various switches and valves. The plasma formation is preferably initiated through the coupling of an oscillating field to the plasma chamber. Many processed gas mixtures can be used. The preferred processed gas mixture comprises a mixture of twenty-five percent oxygen and seventy-five percent argon. The oxygen chemically reacts with hydrocarbons on the specimen and specimen holder and converts them to $CO_2$ and $H_2O$. The argon provides the means to reduce specimen amorphous damage.

54 Claims, 4 Drawing Sheets

PLASMA PROCESSING SYSTEM FOR TRANSMISSION ELECTRON MICROSCOPY SPECIMENS AND SPECIMEN HOLDERS

BACKGROUND OF THE INVENTION

1. Field of the Invention

The present invention relates to a plasma processing system for Transmission Electron Microscopy, or TEM, specimens and specimen holders. More specifically, the system utilizes a low energy, high frequency or HF, plasma to remove amorphous damage resulting from various specimen preparation techniques from TEM specimens and to remove contamination from TEM specimens and specimen holders.

2. Description of the Prior Art

Transmission Electron Microscopy, or TEM, technology enables materials to be analyzed at near atomic resolution by providing high magnification, high resolution imaging and analysis capabilities. TEM enables scientists to gather information relating to a material's physical properties such as its microstructure, crystalline orientation and elemental composition. This information has become increasingly important as the need for advanced materials for use in areas such as microelectronics and optoelectronics, biomedical technology, aerospace, transportation systems and alternative energy sources, among others, increases.

TEM is accomplished by examining material specimens under a transmission electron microscope. In a transmission electron microscope, a series of electro-magnetic lenses direct and focus an accelerated beam of electrons, emitted from an electron gun contained within the microscope, at the surface of a specimen. Electrons transmitted through the specimen yield an image of the specimen's structure which provides information regarding its properties. In addition, elemental and chemical information is provided by both the transmitted electrons and the x-rays that are emitted from the specimen's surface as a result of electron interaction with the specimen. Thus, because it is necessary for the electron beam to transmit through the specimen, a key component of successful material analysis by TEM techniques is the condition and preparation of the specimen itself.

Before a specimen can be analyzed using TEM, it must be prepared using various techniques to achieve the necessary electron transparency. This electron transparency is accomplished by thinning a defined area of the specimen. For equal resolution, the required thickness of the specimen is dependent on the accelerating voltage of the transmission electron microscope. For a 120 kV microscope, the specimen thickness must be on the order of 100 to 2000 angstroms. A 1,000 kV microscope can tolerate a specimen thickness of up to 5,000 angstroms.

Specimens are prepared through several well known methods, including, but not limited to, electrolytic thinning, mechanical grinding, ultramicrotomy, crushing, and ion milling. Often times, multiple methods are utilized to prepare a single specimen. For most types of specimens, either electrolytic thinning or ion milling is used as the final form of specimen preparation. In both cases, amorphous damage ranging in thickness from 1–10 nanometers may result, particularly in the case of ion milling. In this case, the energy of the ion beam transforms the crystalline structure of the material to an amorphous state. This amorphous damage adversely effects the quality of the TEM analysis because it alters the natural characteristics of the material.

Once prepared, the specimen is placed into the microscope's specimen holder, which is an individual component separate from and external to the microscope itself. The specimen holder is then inserted into a goniometer located within the column of the microscope. The goniometer provides X-Y-Z and tilt manipulation of the specimen and places the specimen between the lenses of the microscope.

In addition to amorphous damage resulting from the preparation process, another problem which adversely affects the quality of the TEM analysis is hydrocarbon contamination of the specimen and specimen holder. This contamination can occur as a result of poor operator handling techniques during the preparation process, such as touching the specimen and/or specimen holder with an ungloved hand. Other contamination may result from subjecting the specimen to an ion milling system that utilizes an oil diffusion pump whereby backstreaming of oil will lead to contamination, the use of hydrocarbon based solvents and adhesives in the preparation process, storage of the specimen holder in ambient conditions, and repeated exposure to the microscope's vacuum system which may contain oil vapor which has migrated up the electron optics column from an oil diffusion pump. Although contamination of specimens mainly consists of hydrocarbon compounds, other types of contamination, such as oxides or particulates, can be present.

Furthermore, in recent years, transmission electron microscope manufacturers have increased the current density of the electron beam through advancements in electron gun technology. Beam current density increases with the brightness of the gun as shown in Table I.

TABLE I

| Type of Gun Technology: | Beam Current (for a 10 angstrom probe size): |
| --- | --- |
| Tungsten Filament | 1 to 1.5 picoamps |
| $LaB_6$ | 10 to 15 picoamps |
| Field Emission Gun (FEG) | 0.5 to 0.6 nanoamps |

With increased brightness and electron beam current density comes increased resolution and enhanced analytical capabilities. However, increasing brightness and beam current also increases the localized energy of the electron beam, which, in turn, increases the attraction of hydrocarbon compounds to the beam. As a result, as the brightness and electron beam current density increase, so does the tendency for the hydrocarbon contamination to migrate to the impingement point of the electron beam on the specimen. As this migration occurs, carbon formations obstruct that particular area of the specimen from both image observation and the possibility of acquisition of analytical information. Thus, with increased brightness and electron beam current density comes an increased need for a contamination-free specimen.

Richard S. Thomas and John R. Hollohan, in an article entitled "Use of Chemically-Reactive Gas Plasmas in Preparing Specimens for Scanning Electron Probe Microanalysis", Proceeding of the 7th Annual Scanning Electron Microscope Symposium, Scanning Electron Microscopy, pp. 84–89, 1974, disclosed the use of an oxygen plasma for etching and ashing scanning electron microscopy, or SEM, specimens and for cleaning carbonaceous material from SEM specimens and instrument parts. The use of a pure oxygen plasma, however, was not demonstrated to have reduced the amorphous damage of all specimens.

H. W. Zandbergen, et al., "The Use of Plasma-Cleaning for the Preparation of Clean Electron-Transparent Thin Foils," Proceeding of the XIII International Congress for Electron Microscopy, Volume 1, pp. 1003–1004, 1994, discloses the use of plasma cleaning, specifically low energy argon plasma, for the reduction of the amorphous layer and carbon contamination in TEM specimens, the latter being shown to be reduced by a factor of 100.

Furthermore, it is well known in the art to use a plasma generated from ambient air, which essentially comprises an approximate mixture of 80% nitrogen and 20% oxygen, for processing of TEM specimens.

What is not disclosed, however, and thus what is lacking in the prior art is an integrated processing method and apparatus therefor which may be used prior to a specimen's insertion into a transmission electron microscope that removes both amorphous damage and contamination from TEM specimens and specimen holders.

SUMMARY OF THE INVENTION

A plasma processing method and apparatus are disclosed in which a low energy HF plasma is preferably used to remove both amorphous damage resulting from various specimen preparation techniques and contamination, mainly in the form of hydrocarbons, from TEM specimens and specimen holders. The system is preferably a totally self-contained system which a comprises a vacuum system, a plasma chamber into which the specimen and the specimen holder are inserted, a housing having an access port with removable inner sleeve components and an HF power supply which is coupled to the plasma chamber and enables both the generation and maintenance of the plasma. The inner sleeve components are preferably capable of accepting specimen holders produced by all manufacturers of transmission electron microscopes.

To commence processing, the vacuum system is engaged for the evacuation of the plasma chamber for subsequent formation of the plasma. Process gas may be introduced into the plasma chamber through the automated operation of various switches and valves. Plasma formation is preferably initiated through the coupling of an oscillating field to the plasma chamber. Many process gas mixtures can be used, including a mixture of a noble gas and an oxidant. More particularly, a 25% oxygen and 75% argon mixture is preferred. The oxygen chemically reacts with carbonaceous substances on the specimen and specimen holder and converts them to $CO_2$ and $H_2O$. The argon provides the means to reduce specimen amorphous damage.

These and other advantages and features of the present invention will be more fully understood with reference to the presently preferred embodiments thereof and to the appended drawings.

DESCRIPTION OF THE PREFERRED EMBODIMENTS

Figure 1:
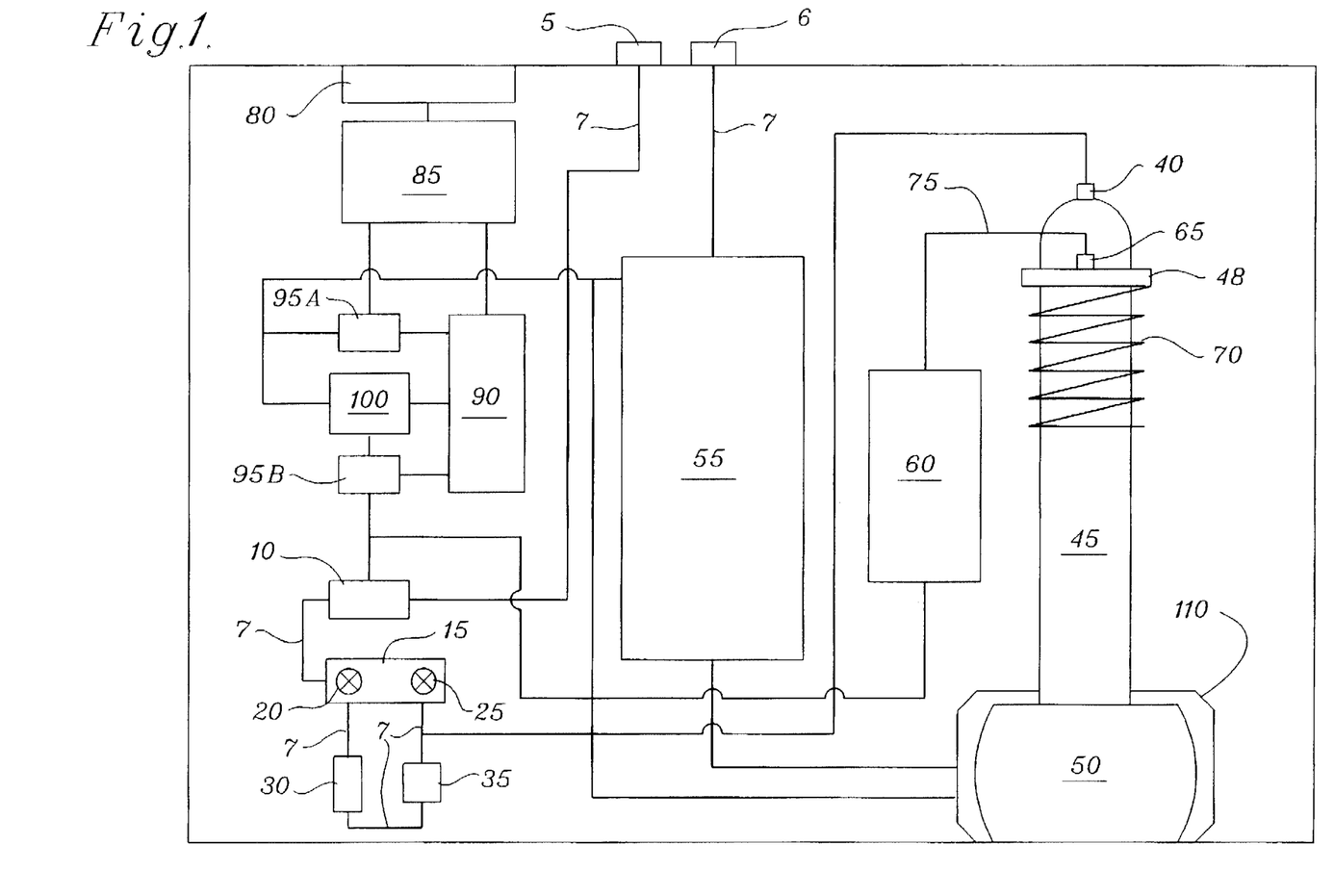
FIG. 1 is a diagrammatic view of the system.

Referring now to FIG. 1, the process gas is connected to process gas inlet bulkhead fitting 5 located on the external surface of the system. Gas flow through the system from component to component is accomplished by using tubing 7, which is preferably constructed of stainless steel, although other types of tubing such as tygon, reinforced plastic, copper and polyethylene could also be utilized. From process gas inlet bulkhead fitting 5, gas flow is through pressure regulator 10, which regulates the gas inlet pressure to the system, manifold 15 containing gas valve 20 and vent valve 25, filter 30, which removes any particulate contamination; and finally, metering valve 35 to plasma chamber gas inlet port 40 located on plasma chamber 45. Gas valve 20 and vent valve 25 are electrically operated solenoid valves. Gas valve 20 controls the flow of process gas into plasma chamber 45 while vent valve 25 controls venting of the system to ambient with process gas for the removal and exchange of specimens and specimen holders.

Figure 2:
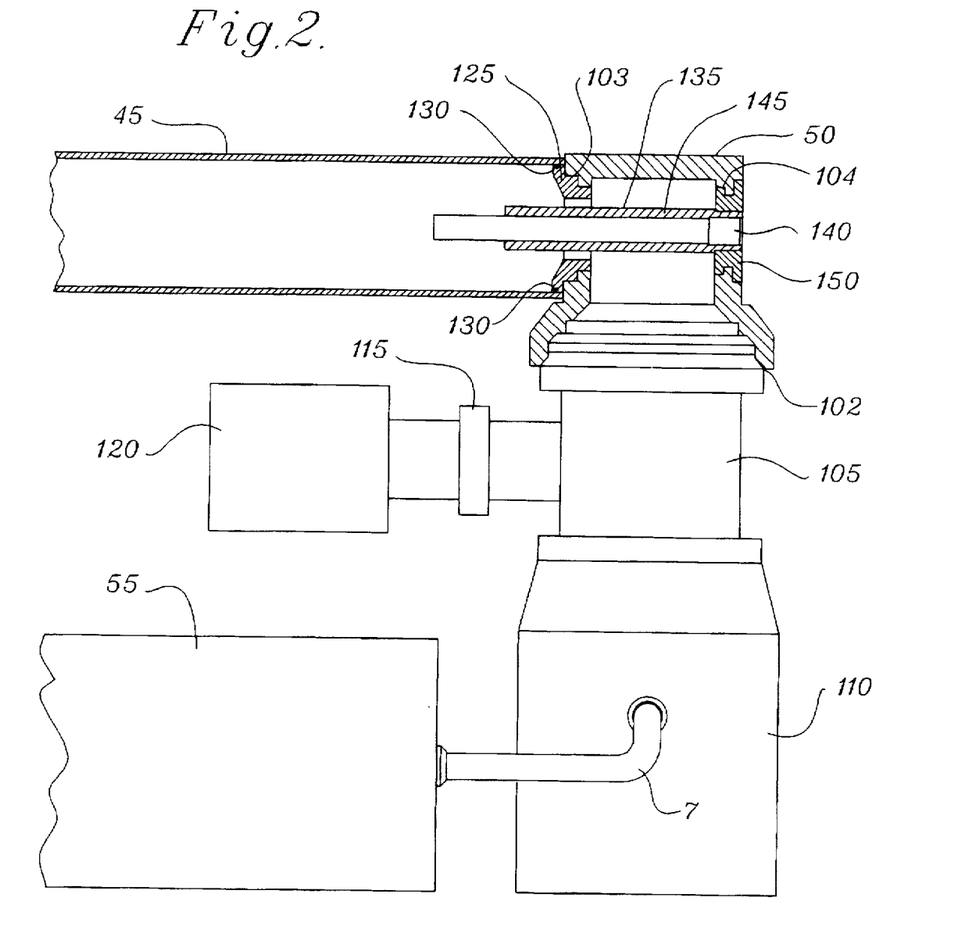
FIG. 2 is a side view of a portion of the system showing the plasma chamber, housing, and vacuum system.

Referring now to FIGS. 1 and 2, plasma chamber 45 is a hollow cylindrical tube preferably fabricated from quartz tubing. Quartz tubing is preferable because of its ability to tolerate high temperatures without damage, and its ability to avoid etching with prolonged use. Although quartz tubing is preferred, other materials with similar characteristics may be used. Plasma chamber 45 is supported by standoff 48. Located on the end of plasma chamber 45 opposite plasma chamber gas inlet port 40 is housing 50. As seen in FIG. 2, located on housing 50 are drag pump access port 102, plasma chamber access port 103, and specimen holder port 104. Connected to drag pump access port 102 is heat exchanger flange 105, which in turn is connected to molecular drag pump 110. Molecular drag pump 110 provides a suitable vacuum level for the generation and maintenance of the plasma by providing an ultimate vacuum of $10^{-6}$ torr in plasma chamber 45. Molecular drag pump 110 will not operate properly unless its outlet is pre-pumped. Thus, for proper operation of molecular drag pump 110, it is necessary to reduce its foreline or outlet vacuum. This task is accomplished by backing molecular drag pump 110 with four stage, oil-free diaphragm pump 55. As seen in FIGS. 1 and 2, diaphragm pump 55 is connected to the outlet of molecular drag pump 110 by flexible tubing 7. The oil-free system is preferred to eliminate the possibility of introducing hydrocarbon contamination from the lubricating oil of the pump into plasma chamber 45 and housing 50 during processing. The use of a diaphragm pump in connection with a molecular drag pump is well known in the prior art.

Heat exchanger flange 105 is a hollow cylinder made of thin wall stainless steel tubing and is used to promote convective heat transfer, thereby preventing the heat generated by the operation of molecular drag pump 110 from being conducted to housing 50 and plasma chamber 45. Heat exchanger flange 105 is utilized to keep specimens and specimen holders which are being processed at a temperature close to ambient temperature. This is preferred because rapid insertion of the specimen into the microscope after processing is required. The fact that the specimen is close to ambient temperature minimizes the thermal drift of the specimen and specimen holder and minimizes the time needed for the system to equilibrate. Vacuum gauge 120 is connected to heat exchanger flange 105 through vacuum port 115 and allows the monitoring of the system vacuum to ensure that a suitable vacuum for plasma formation is achieved. The plasma may be generated at an approximate vacuum of 10 mtorr.

Plasma chamber access port 103 provides the access from plasma chamber 45 to housing 50 and is simply a means of connecting plasma chamber 45 to housing 50 which facilitates easy removal of plasma chamber 45 for cleaning. Plasma chamber flange 125 is attached to plasma chamber access port 103 and provides, along with O-ring 130, a vacuum tight seal of plasma chamber 45 onto housing 50.

Figure 3:
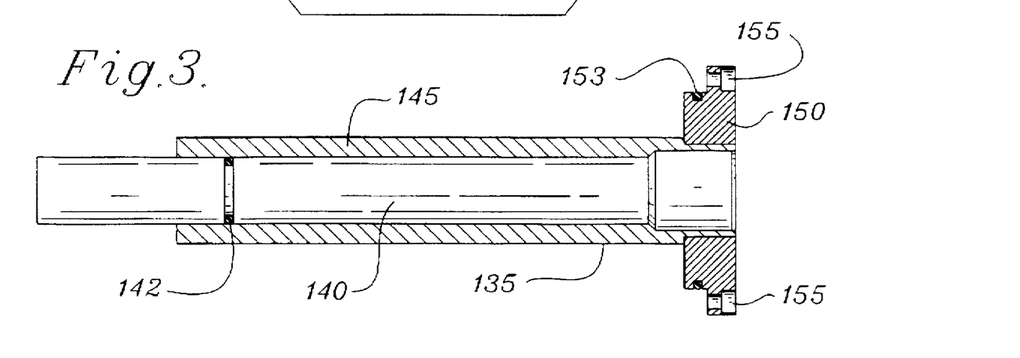
FIG. 3 is a sectional view of the specimen holder sleeve assembly.

Specimen holders vary in size and configuration according to manufacturer. Thus, rather than manufacture a separate plasma chamber 45 and housing 50 to fit each, a detachable, interchangeable specimen holder sleeve assembly 135, as shown in FIGS. 2 and 3, has been developed which is capable of accommodating specimen holders of all varieties. Specimen holder sleeve assembly 135 consists of specimen holder sleeve 145 which is affixed to specimen holder flange 150. Specimen holder sleeve 145 has a constant outer diameter and an inner diameter sized and adapted to accept specimen holders of various sizes and configurations. Specimen holder flange 150 is fabricated to fit specimen holder port 104. Thus, specimen holder sleeve assembly 135 fits into housing 50, as shown in FIG. 2, and is fastened in place with screws 155. Specimen holder flange 150 and O-ring 153 provide a vacuum tight seal of specimen holder sleeve assembly 135 to housing 50. Specimen holder 140 can then be slip fit into specimen holder sleeve 145 with a vacuum tight seal being provided by O-ring 142 of specimen holder 140. When in position, the portion of specimen holder 140 which contains the specimen itself is extended into plasma chamber 45 and is exposed to the plasma for processing, as shown in FIGS. 2 and 3. The system is provided with a number of specimen holder sleeve assemblies, each having a different specimen holder sleeve 145 sized to fit a specimen holder of a particular manufacturer. Thus, a user can process specimens using specimen holders of varying manufacturers simply by interchanging specimen holder sleeve assembly 135.

Plasma is initiated through the coupling of an oscillating field to plasma chamber 45 into which the process gas flows. Referring now to FIG. 1, power entry module 80 provides system access to external power. Power entry module 80 is a multi-voltage tapped receptacle that can be jumper selected to accept power inputs of 100, 120, 220, 230 and 240 VAC. This jumper selecting capability allows the system to be operated in any country regardless of that country's voltage standard without having to rewire the system. Thus, the same system can be operated in Japan, where the standard voltage is 100 VAC, England, where the standard voltage is 240 VAC, and Korea, where the standard voltage is 220 VAC, simply by presetting power entry module 80. The output of power entry module 80 is connected to the input of multi-tapped transformer 85. Transformer 85 outputs 6.3 VAC, 32 VAC, and 120 VAC regardless of the voltage connected to its input because it contains multiple input taps which accept inputs of 100, 120, 220, 230 and 240 VAC. The correct tap of transformer 85 is connected according to the setting of power entry module 80.

The 6.3 VAC and 32 VAC outputs of transformer 85 are connected to the input of system power supply 90. Both the 6.3 VAC and 32 VAC are regulated by system power supply 90. The 6.3 VAC is rectified and converted into a +5 V DC signal by system power supply 90. The +5 V DC signal is used to drive the system logic. Similarly, the 32 VAC is rectified and converted into a ±15 V DC signal by system power supply 90. The ±15 V DC signal is used to drive the system amplifiers.

The 120 VAC output of transformer 85 is connected to the output of relay 95A. The output of relay 95A is used to drive the vacuum system and thus is connected to the power inputs of molecular drag pump 110 and diaphragm pump 55. Relay 95A is switched to the on position when the vacuum system is to be turned on. The output of relay 95A is also connected to the input of electro-magnetic interference, or EMI, filter 100. EMI filter 100 prevents the radio frequency interference and other voltage transients generated internal to the system from being transmitted externally. The output of EMI filter 100 is connected to the input of relay 95B. The output of relay 95B is connected to and used to drive HF power supply 60. Thus, relay 95B is engaged when HF power supply 60 is to be engaged.

Figure 4:
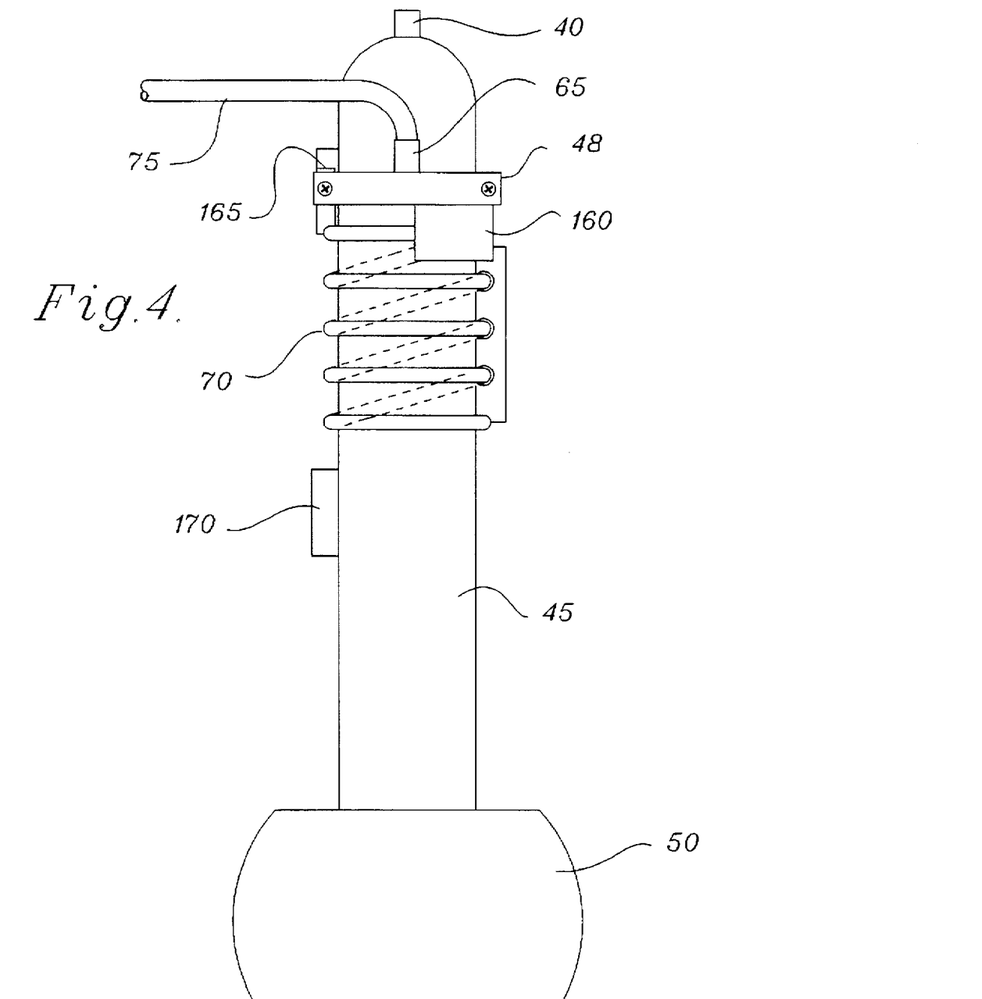
FIG. 4 is a top plan view of a portion of the system showing the coupling of the HF power supply to the plasma chamber.

HF power supply 60 provides the oscillating field that is used to generate the plasma and is physically and electrically coupled to plasma chamber 45. As shown in FIG. 4, the output of HF power supply 60 is connected to BNC connector 65 located on plasma chamber 45 by co-axial cable 75. BNC connector 65 is connected to variable capacitor 160 which in turn is connected to one end of HF antenna 70. Finally, the opposite end of HF antenna 70 is connected to ground connector 165. This configuration is a common technique for HF plasma generation and allows for both capacitive and inductive coupling. For cleaning of TEM specimens, inductive coupling is considered to be preferable since less heat is generated. There may be some instances, however, in which capacitive coupling is preferred, such as when a higher temperature processing is desired because of specimen characteristics.

For effective HF power generation, the power circuitry should be matched to plasma chamber 45 in terms of inductance and capacitance in order to minimize the reflected power of the system. By minimizing the reflected power of the system, the overall electrical efficiency of the system is increased. In virtually all cases, matching networks are included as integral components of the HF power supply system.

The preferred frequency to be used by HF power supply 60 is 13.56 mHz. This frequency is an industrial frequency set aside by the FCC for applications similar to the one described herein and is commonly employed in industrial plasma generation. The frequency, however, of the power supply 60 is not limited technically thereto, but may be classified as HF at any frequency greater than 60 Hz.

For general applications, a process gas consisting of a mixture of 25% oxygen and 75% argon is recommended. Oxygen chemically reacts with the hydrocarbon contamination on the specimen and specimen holder and converts it to $CO_2$ and $H_2O$, which is evacuated by molecular drag pump 110 and diaphragm pump 55 through exhaust port 6. Argon provides the means to reduce amorphous damage on the specimen resulting from preparation of the specimen. A process gas consisting solely of oxygen may also be used. Such a process gas will result in faster processing than the oxygen and argon mixture but will not remove the amorphous layer as effectively. Also, other reactive gases, such as iodine and chlorine, may be used as the process gas, or components thereof, and should be chosen depending upon the material to be processed and the contaminant to be removed.

The system employs a low energy, non-equilibrium HF plasma in which mobile, free-electrons are accelerated to high velocities by the oscillating electromagnetic field that excites the process gas atoms and creates the plasma. Use of such a plasma for processing increases the temperature of the material being processed typically to only a few degrees above ambient temperature. The fact that the processing is effected without any significant heating of the specimen is preferable because excessive heating of the specimen may alter the properties of the material.

Figure 5:
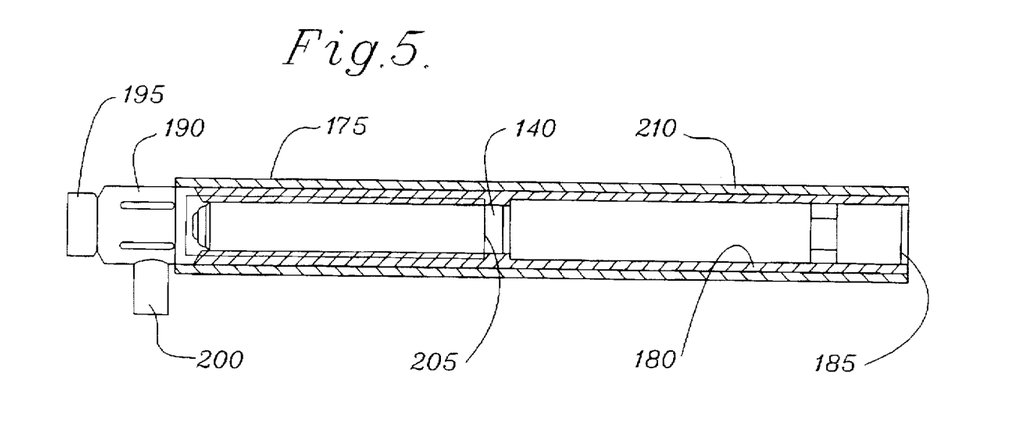
FIG. 5 is a plan view, partially in section, of the vacuum storage enclosure.

Referring now to FIG. 5, following cleaning of the specimen and specimen holder, a separate, stand alone vacuum storage enclosure 175 is used to store the specimen and specimen holder under clean, vacuum conditions. Vacuum storage enclosure 175 consists of internal tube 180 with receptacle 185 located on one end to accept specimen holder 140 and two-position vacuum valve 190 located on the opposite end. When knob 195 of two-position vacuum valve 190 is in the open position, the internal volume of the container is exposed for vacuum evacuation. Evacuation port 200 provides the means through which the vacuum evacuation of vacuum storage enclosure 175 may be accomplished. When knob 195 is in the closed position, a vacuum is maintained in vacuum storage enclosure 175. Located at the end of vacuum storage enclosure 175 nearest to two-position vacuum valve 190 is sight glass 205 which enables the direct observation of the specimen at the tip of specimen holder 140. Protective sleeve 210, preferably fabricated from a high impact polymer, protects vacuum storage enclosure 175, and thus the specimen and specimen holder 140, against inadvertent impact.

Figure 6:
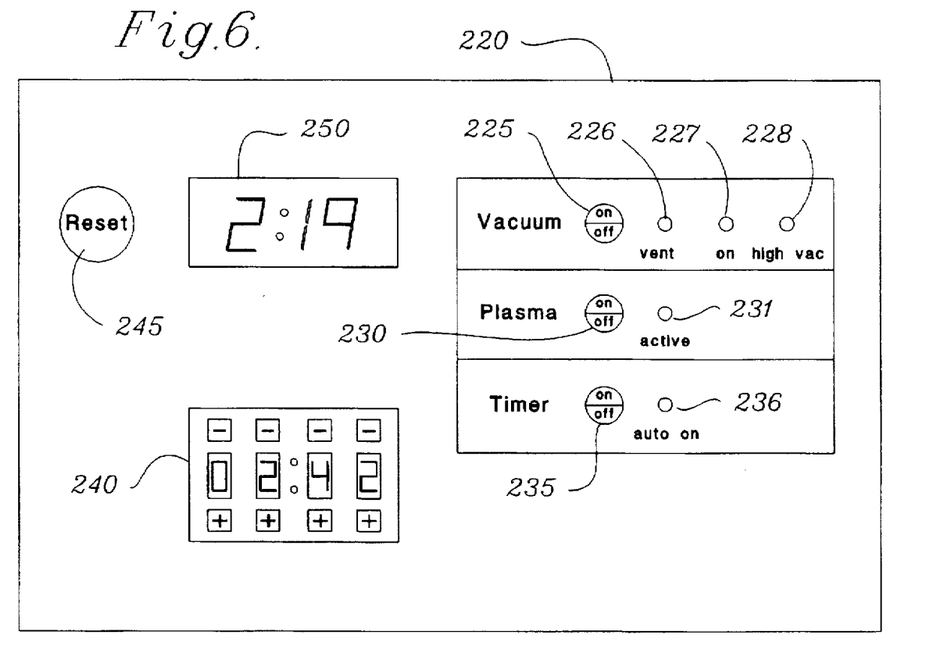
FIG. 6 is a diagrammatic view of the front panel key pad.

The system is preferably self-contained in an enclosure that houses all the components that have been described herein. The specimen and specimen holder 140 are inserted into plasma chamber 45 for processing by inserting same into specimen holder sleeve assembly 135 through specimen port 104. As described above, a vacuum seal is formed by O-rings 142 and 153. Key pad 220 contains a number of system controls consisting of vacuum switch 225, plasma switch 230, mode selection switch 235, timer switch 240 and reset switch 245. When vacuum switch 225 is engaged, the vacuum system consisting of molecular drag pump 110 and diaphragm pump 55 is activated for the evacuation of plasma chamber 45 for subsequent formation of plasma. When vacuum switch 225 is disengaged, vent valve 25 is opened to vent the system to atmospheric pressure. Visual indications are provided when the system is vented, when the vacuum system is energized, and when a suitable vacuum level has been achieved in plasma chamber 45 by LED indicators 226, 227 and 228, respectively, located on key pad 220. Plasma switch 230 controls gas valve 20 which, when engaged, allows process gas to flow into plasma chamber 45. Plasma switch 230 also activates HF power supply 60 for the creation of the plasma. As shown in FIG. 4, photo detector 170 located on the surface of plasma chamber 45 senses the presence of plasma and provides a visual indication of same to the front panel through LED indicator 231. Mode selection switch 235 permits selection between system operation in the manual or automatic mode. In the manual mode, the plasma is energized and de-energized solely at the discretion of the operator. In the automatic mode, a timer is enabled which permits processing for a pre-determined duration. Process time is entered through indexable timer switch 240. The timer is initiated when the plasma is energized. Elapsed processing time is indicated on display 250. Reset switch 245 zeros the timer and de-energizes the plasma by de-activating HF power supply 60. When processing is complete, specimen holder 140 may be removed for immediate TEM analysis or storage in vacuum storage enclosure 175.

Figure 7:
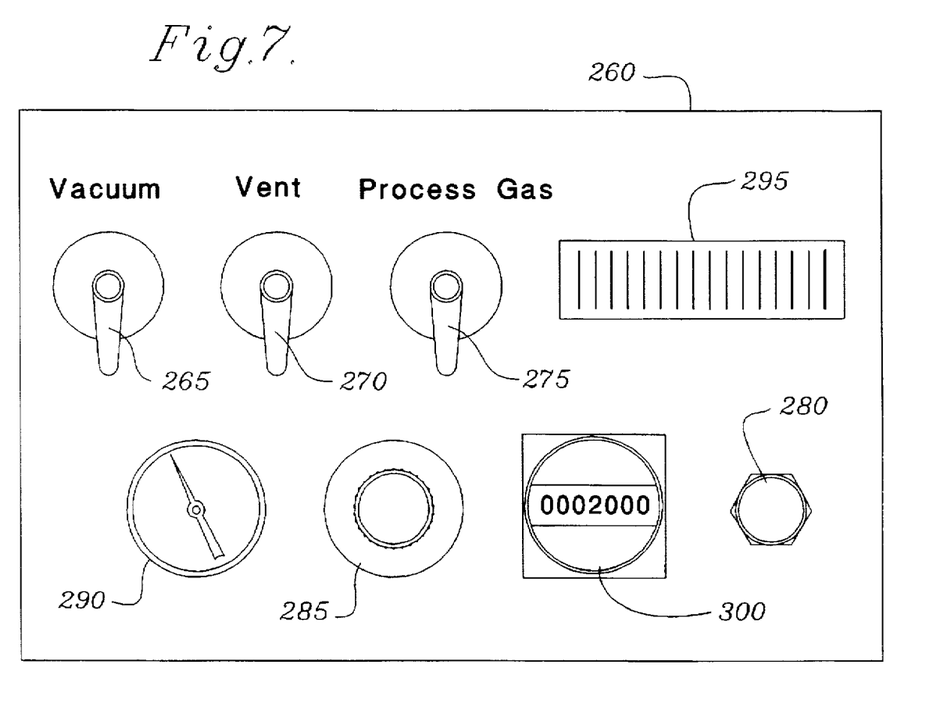
FIG. 7 is a diagrammatic view of the service panel.

Also located on the front panel of the enclosure is service panel 260. Service panel 260 is a diagnostic tool which may be used to monitor system operation and manually bypass and override system controls. Located on service panel 260 are vacuum switch 265, vent switch 270, and process gas switch 275, which may be used to manually activate and deactivate the vacuum system, vent valve, and process gas flow, respectively. Process gas valve control 280 may be used to manually operate gas valve 20 and adjust the flow of process gas to plasma chamber 45. Pressure regulator control 285 may be used to manually operate pressure regulator 10 while pressure gauge 290 monitors the process gas pressure being supplied to metering valve 35. Vacuum level display 295 is connected to vacuum gauge 120 and provides a bar graph indication of the vacuum level. Hour meter 300 indicates the total elapsed time that the vacuum system has been operating.

While a present preferred embodiment of the invention is described, it is to be distinctly understood that the invention is not limited thereto but may be otherwise embodied and practiced within the scope of the following claims.

What is claimed is:

1. A plasma processing apparatus for removing at least one of contamination and damage from at least one of transmission electron microscopy specimens and specimen holders, comprising:

(a) a plasma chamber into which a preselected process gas is flowed and into which at least one of a specimen and specimen holder are inserted;

(b) an oil-free vacuum system for evacuating said plasma chamber; and (c) an oscillating field generated adjacent said plasma chamber, said oscillating field and said preselected process gas combining to form a low energy, high frequency plasma within said plasma chamber.

2. An apparatus according to claim 1, wherein said low energy, high frequency plasma impinges upon said at least one of said specimen and specimen holder wherein said at least one of said contamination on and damage to said at least one of said specimen and specimen holder are reduced.

3. An apparatus according to claim 1, wherein said process gas comprises a combination of gas elements.

4. An apparatus according to claim 3, wherein one element of said combination of gas elements is a noble gas.

5. An apparatus according to claim 4, wherein the noble gas is argon.

6. An apparatus according to claim 3, wherein one element of said combination of gas elements is an oxidant.

7. An apparatus according to claim 6, wherein the oxidant is oxygen.

8. An apparatus according to claim 3, wherein one element of said combination of gas elements reduces the contamination to said at least one of said specimen and specimen holder.

9. An apparatus according to claim 3, wherein one element of said combination of gas elements reduces the damage to said at least one of said specimen and specimen holder.

10. An apparatus according to claim 3, wherein oxygen comprises 25 percent of said combination of gas elements.

11. An apparatus according to claim 3, wherein argon comprises 75 percent of combination of gas elements.

12. An apparatus according to claim 1, wherein said plasma chamber is constructed to withstand high temperature applications.

13. An apparatus according to claim 12, wherein said plasma chamber is constructed from a silicon-based material.

14. An apparatus according to claim 13, wherein said silicon-based material is quartz.

15. An apparatus according to claim 1, wherein the oil-free vacuum system comprises a molecular drag pump backed by a diaphragm pump.

16. An apparatus according to claim 1, further comprising a means for generating said oscillating field adjacent said plasma chamber.

17. An apparatus according to claim 1, wherein a means for generating said oscillating field comprises a coupling means.

18. An apparatus according to claim 17, wherein said coupling means is inductive.

19. An apparatus according to claim 17, wherein said coupling means is capacitive.

20. An apparatus according to claim 17, wherein said oscillating field is generated by a high frequency power supply and said coupling means comprises:
   (a) connecting means connected to said high frequency power supply;
   (b) a capacitor means connected to said connecting means; and
   (c) a high frequency antenna mounted exterior to and adjacent said plasma chamber having a first end and a second end, the first end of said high frequency antenna connected to capacitor means, the second end of said high frequency antenna connected to ground.

21. An apparatus according to claim 20, wherein said capacitor means comprises a variable capacitor.

22. An apparatus according to claim 20, wherein said high frequency antenna is mounted circumferentially to said plasma chamber.

23. An apparatus according to claim 20, wherein said high frequency power supply operates at a frequency of 13.56 mHz.

24. An apparatus according to claim 1, wherein said plasma chamber is circular in section.

25. An apparatus according to claim 1, further comprising a housing removably affixed to said plasma chamber and a specimen holder sleeve assembly mountable onto said housing into which specimen holders of preselected sizes and configurations can be inserted.

26. An apparatus according to claim 25, wherein said specimen holder sleeve assembly comprises:
   (a) a flange mountable onto said housing;
   (b) a cylindrical sleeve having a first end and a second end and having preselected interior space which is sized and adapted to accept interchangeable specimen holders, the first end of said cylindrical sleeve being affixed to said flange and the second end of said cylindrical sleeve being open; and
   (c) a means for providing a vacuum tight seal between said flange and said housing and between said specimen holder and said cylindrical sleeve.

27. An apparatus according to claim 26, wherein said sealing means comprises an O-ring.

28. An apparatus according to claim 1, further comprising a vacuum storage enclosure for storing said at least one of said specimen and specimen holder in a vacuum environment.

29. An apparatus according to claim 28, wherein said vacuum storage enclosure comprises:
   (a) a tube having a first end, a second end and an internal chamber, said internal chamber constructed to accept said at least one of said specimen and specimen holder;
   (b) a receptacle located at said first end of said tube through which said at least one of said specimen and specimen holder are inserted;
   (c) a valve means located at said second end of said tube which can be operated between a first position and a second position, wherein said first position provides a vacuum tight seal of said internal chamber and said second position exposes said internal chamber for evacuation, said valve means having an evacuation port through which the vacuum evacuation of said vacuum storage enclosure is accomplished; and
   (d) a protective sleeve mounted adjacent said tube.

30. An apparatus according to claim 29, wherein said valve means comprises a two-position vacuum valve.

31. An apparatus according to claim 29, further comprising a means for observing said at least one of said specimen and specimen holder adjacent said valve means.

32. An apparatus according to claim 31, wherein said observing means comprises a sight glass.

33. An apparatus according to claim 29, wherein said protective sleeve comprises a high impact polymer.

34. A method of removing at least one of contamination and damage from at least one of transmission electron microscopy specimens and specimen holders comprising the steps of:
   (a) placing said at least one of said specimen and specimen holder in a sealed chamber;
   (b) evacuating said chamber of ambient air in an oil-free environment;
   (c) flowing a preselected process gas into said chamber;
   (d) forming a low energy, high frequency plasma from said preselected process gas within said chamber; and
   (e) causing said low energy, high frequency plasma to impinge upon said at least one of said specimen and specimen holder such that said at least one of said contamination and damage are reduced.

35. A method according to claim 34, wherein said damage is amorphous damage.

36. A method according to claim 34, wherein said contamination comprises hydrocarbon contamination.

37. A method according to claim 34, wherein said chamber is fabricated from a material specifically selected for use in high temperature applications.

38. A method according to claim 37, wherein the material specifically selected for use in high temperature applications is silicon-based.

39. A method according to claim 38, wherein the silicon-based material is quartz.

40. A method according to claim 34, wherein said preselected process gas comprises a combination of gas elements.

41. A method according to claim 40, wherein one element of said combination of gas elements is a noble gas.

42. A method according to claim 41, wherein the noble gas is argon.

43. A method according to claim 40, wherein one element of said combination of gas elements is an oxidant.

44. A method according to claim 43, wherein the oxidant is oxygen.

45. A method according to claim 40, wherein at least one element of said combination of gas elements reduces said contamination.

46. A method according to claim 40, wherein at least one element of said combination of gas elements reduces said damage.

47. A method according to claim 40, wherein argon comprises 75 percent of said combination of gas elements.

48. A method according to claim 40, wherein oxygen comprises twenty-five percent of said combination of gas elements.

49. A method according to claim 34, wherein said evacuating step is performed by an oil-free vacuum system.

50. A method according to claim 49, wherein said oil-free vacuum system comprises a molecular drag pump backed by a diaphragm pump.

51. A method according to claim 34, further comprising the additional step of coupling an oscillating field to said chamber.

52. A method according to claim 51, wherein said coupling step utilizes an inductive field.

53. A method according to claim 51, wherein said coupling step utilizes a capacitive field.

54. A method according to claim 51, wherein said oscillating field is generated by a high frequency power supply and said coupling is performed by a coupling means, said coupling means comprising:

(a) a connecting means connected to said high frequency power supply;

(b) a variable capacitor connected to said connecting means; and (c) a high frequency antenna mounted exterior to said chamber having a first end and a second end, the first end of said high frequency antenna connected to said variable capacitor, the second end of said high frequency antenna connected to ground.

* * * * *

UNITED STATES PATENT AND TRADEMARK OFFICE
CERTIFICATE OF CORRECTION

PATENT NO. : 5,633,502
DATED : May 27, 1997
INVENTOR(S) : Paul E. Fischione It is certified that error appears in the above-identified patent and that said Letters Patent is hereby corrected as shown below:

In the abstract:

Line 23, "Many processed gas mixtures" should read -- Many process gas mixtures --.

Line 24, "The preferred processed gas mixture" should read -- The preferred process gas mixture --.

Column 3, line 25, "which a comprises" should read -- which comprises --.

In the claims:

Column 8, line 20, "specimens" should read -- specimen --.

Column 8, line 56, after "75 percent of" insert -- said --.

Signed and Sealed this

Thirtieth Day of September, 1997

Attest:

BRUCE LEHMAN

*Attesting Officer*    Commissioner of Patents and Trademarks